United States Patent [19]

Hesson

[11] Patent Number: 5,032,597

[45] Date of Patent: Jul. 16, 1991

[54] METHOD OF USING PHENYLQUINOLINECARBOXYLIC ACIDS AND DERIVATIVES FOR LYMTHOID LEUKEMIA TREATMENT IN A MAMMAL

[75] Inventor: David P. Hesson, Wilmington, Del.

[73] Assignee: Du Pont Merck Pharmaceutical, Wilmington, Del.

[21] Appl. No.: 30,421

[22] Filed: Mar. 26, 1987

Related U.S. Application Data

[60] Division of Ser. No. 727,808, Apr. 26, 1985, Pat. No. 4,680,299, which is a continuation-in-part of Ser. No. 605,104, Apr. 30, 1984, abandoned, which is a continuation-in-part of Ser. No. 516,319, Jul. 22, 1983, abandoned.

[51] Int. Cl.$^5$ .................... A61K 31/47; A61K 31/41

[52] U.S. Cl. .................... 514/311; 514/314; 514/312

[58] Field of Search .................... 514/314, 311, 312

[56] References Cited

PUBLICATIONS

Dexter, D. L. et al Cancer Research 75:5563–68, Nov. 1985.

A. Goldin et al, Recent Results Cancer Res. 76:176–191 (1981).

Primary Examiner—David B. Springer

[57] ABSTRACT

Phenylquinolinecarboxylic acids and derivatives thereof, such [as] 2-(2'-fluoro-1,1'-biphenyl-4-yl)-6-fluoro-3-methyl-4-quinolinecarboxylic acid, or a sodium or potassium salt thereof, are useful as tumor inhibiting agents.

11 Claims, No Drawings

METHOD OF USING PHENYLQUINOLINECARBOXYLIC ACIDS AND DERIVATIVES FOR LYMTHOID LEUKEMIA TREATMENT IN A MAMMAL

This is a division of application Ser. No. 727,808, filed Apr. 26, 1985, now U.S. Pat. No. 4,680,299, which in turn is a continuation-in-part of U.S. application Ser. No. 605,104, filed Apr. 30, 1984, now abandoned, which is a continuation-in-part of U.S. application Ser. No. 516,319, filed July 22, 1983, now abandoned.

BACKGROUND OF THE INVENTION

1. Field of Invention

This invention relates to tumor inhibiting pharmaceutical compositions, methods of inhibiting the growth of mammalian tumors, and phenylquinolinecarboxylic acids and derivatives thereof useful in such compositions and methods.

2. Literature Background

Cinchophen, 2-phenyl-4-quinoline carboxylic acid, has been known for many years and has been described as being useful as an antirheumatic and in the treatment of gout. Cinchophen has the formula:

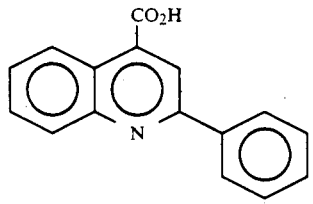

Many cinchophen and cinchoninic acid derivatives have been prepared in investigating the Pfitzinger reaction and for use in color photographic developing.

Buu-Hoi et al. [*J. Chem. Soc.*, 386–8 (1953)] report 2-arylcinchoninic acids, prepared by the Pfitzinger reaction, having the formula:

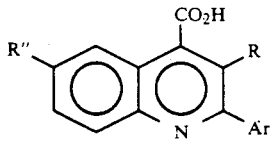

where
R=H, $CH_3$, $C_2H_5$ and phenyl;
Ar=fluoro-substituted phenyl; and
R''=H, Br, Cl or $CH_3$.

No use for these compounds is described.

Epling et al. [Tet. Lett., 23 (38), 3843–3846 (1982)] report

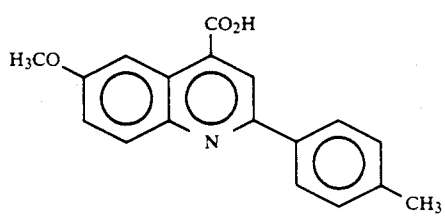

as an intermediate to a new arylmethylsulfonyl chloride convertible to sulfonamides which can be photochemically cleaved.

Starke et al. in U.S. Pat. No. 4,009,020, issued Feb. 22, 1977, describe plant growth regulant cinchoninic acid derivatives, including those of the formula:

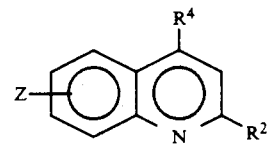

where
Z is H or halogen, preferably H;
$R^2$ is, inter alia, phenyl and halo-substituted phenyl; and
$R^4$ is CN, $CO_2H$ and related esters and amides.

Buu-Hoi et al. [*J. Org. Chem.*, 18, 1209–1224 (1953)] describe 2-arylcinchoninic acids of the formula:

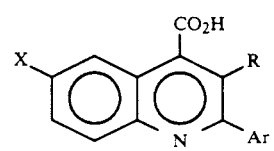

where
X=H or Br;
R=H, $CH_3$, $C_2H_5$ and other groups; and
Ar can be a variety of aromatic groups including 4-biphenylyl, 4-alkylphenyl and 4-phenoxyphenyl.

The compounds prepared were part of a program to investigate the toxicity of cinchoninic acids and quinolines, since cinchophen ("Atophan") can produce a degeneration of liver tissue of a possible precancerous nature. Some of the compounds prepared caused degenerative changes in the liver.

Buu-Hoi et al. [*Rec. trav. Chim.*, 62, 713–718 (1943)] report 2-(41 -cyclohexylphenyl)cinchoninic acid and 2-(4-biphenylyl)cinchoninic acid. Hai et al. [*J. Org. Chem.*, 23, 39–42 (1958)] describe 2(4-cyclopentylphenyl)cinchoninic acids, including 3-methyl and 3-ethyl derivatives, and 6-bromo and 6-methyl derivatives. Buu-Hoi et al. [*J. Org. Chem.*, 22, 668–671 (1957)] report 2-[4-(4-methoxy-3-chlorophenyl)phenyl]cinchoninic acid and its 3-methyl and 3-ethyl derivatives. Another Buu-Hoi report [idem., 24, 39–41 (1959)] describes the 2-methoxy-3-chlorophenyl isomer.

Yen et al. [*J. Org. Chem.*, 23, 1958–1861 (1958)] report 2-phenyl- and 2-(4-fluorophenyl)-6-fluorocinchoninic acids for testing as potential carcinogens.

Steinkopf et al. [Annalen. 540, 7–14 (1939); idem. 543, 119–128 (1940)] report 20(5-methyl- and 5-phenyl-2-thienyl)cinchoninic acids. Sy et al. [*J. Chem. Soc.*, 1975–1978 (1954)]- report 20(5-t-butyl-2-thienyl)cinchoninic acid and its 3-methyl and 6-bromo derivatives.

Buu-Hoi et al. [*Rec. trav. Chim.*, 72, 774–780 (1953)] report 2-[4-(4-hydroxy- and 4-methoxyphenyl)phenyl]cinchoninic acids and their 3-methyl derivatives.

Boykin et al. [*J. Med. Chem.*, 11, 273–277 (1968)] report cinchoninic acids of the formula:

where
R = H, F, CH₃ or OCH₃;
R' = H, CH₃ or CF₃; and
R'' = H, F, Cl, CH₃ or OCH₃.

Although prepared as part of an antimalarial program, it does not appear that these intermediates were tested for antimalarial activity.

Saggiomo et al. [*J. Med. Chem.*, 11, 277–281 (1968)] report antimalarial quinoline-4-methanols derived from the corresponding acids. The latter includes 6,8-dichloro-2-(3-trifluoromethylphenyl)cinchoninic acid and ethyl ester, and 2-(4-chlorophenyl)-6-fluorocinchoninic acid and ethyl ester.

Buu-Hoi et al. [*Rec. trav. Chim.*, 70, 825–832 (1951)] report 2-(4-n-propyl-4'-biphenylyl)cinchoninic acid and 3-methyl-2-(4-ethyl-4'-biphenylyl)cinchoninic acid.

Coles, in U.S. Pat. No. 2,579,420, issued Dec. 18, 1951, describes the conversion of 6,8-dihalocinchoninic acids into 6-halo-8-hydroxycinchoninic acids useful as color formers. Disclosed are compounds of the formula:

→ 8-hydroxy derivatives where
X is Cl or Br;
R₁ is, inter alia, H or lower alkyl; and
R is, inter alia, aryl and heteroaryl, optionally substituted by alkyl, aryl and the like.

Tulagin et al., in U.S. Pat. No. 2,524,741, issued Oct. 3, 1950, describe the use, in color photographic developing, of 8-hydroxyquinolines of the formula:

where
R is halogen, NO₂ or SO₃H;
R₁ can be phenyl or phenyl substituted with Cl, CH₃, OCH₃ or NH₂; and
R₂ can be CO₂H.

French Patent 1,040,440 describes compounds similar to Tulagin et al., useful in color photographic chemistry, of the formula:

where
X is halogen;
R is CO₂H, CONH₂ or CONH-alkyl;
R₁ may be H or lower alkyl; and
R₂ may be aryl or a heterocyclic group.

German Patents 659,496; 668,741; and 668,742 describe 2-phenylcinchoninic acids containing iodo groups and a free or esterified p-hydroxy substituent on the 2-phenyl group. Such compounds are stated to be useful as X-ray contrast agents.

Sakai et al., [Gann, 46, 605–616 (1955)] report that 2-phenyl-4-carboxyquinoline had no tumoricidal effect in in vitro tests using NF mouse sarcoma.

U.S. Pat. No. 2,888,346 issued on May 26, 1959 to Tulagin and Hoffstadt describes compounds of the formula:

where
X¹ is 6-Cl or X¹ is 6-Cl and X² is 8-Br, and their use to protect organic media from damage from ultraviolet radiation.

SUMMARY OF THE INVENTION

According to the present invention there is provided an antitumor pharmaceutical composition consisting essentially of a suitable pharmaceutical carrier and at least one compound having the formula:

$$\text{(I)}$$

wherein

R is

-continued

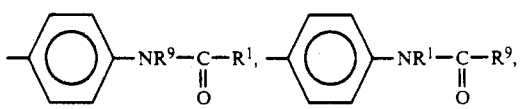

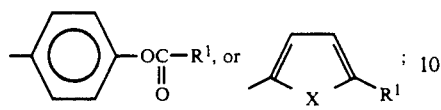

X is O, S(O)$_q$, NH or CH=N;

R$^1$ is CH$_3$CH$_2$(CH$_3$)CH, alkyl of 5–12 carbon atoms, alkenyl of 5–12 carbon atoms, cycloalkyl of 3–7 carbon atoms, cycloalkylalkyl of 5–12 carbon atoms,

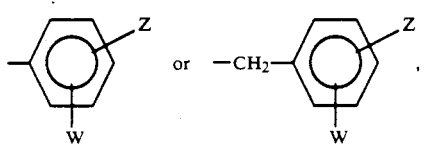

when R is

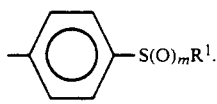

R$^1$ can be in addition alkyl of 3–4 carbon atoms;
R$^2$ is

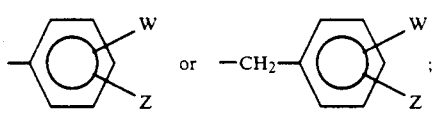

R$^3$ is H, alkoxy of 1–3 carbon atoms, alkylthio of 1–3 carbon atoms or alkyl of 1–2 carbon atoms optionally substituted with one or more of F, Cl, Br or (CH$_2$)$_p$COR$^{10}$ where p is 1, 2, 3 or 4;

R$^4$ is CO$_2$H or CO$_2$R$^{11}$;

R$^5$, R$^6$, R$^7$ and R$^8$ are independently H, F, Cl, Br, I, CH$_3$, CF$_3$, S(O)$_n$R$^{12}$ or CH$_2$CH$_3$, at least two of R$^5$, R$^6$, R$^7$, and R$^8$ being H;

R$^9$ and R$^{9A}$ are independently H or alkyl of 1 to 3 carbon atoms;

R$^{10}$ is OH, OCH$_3$, OCH$_2$CH$_3$, NH$_2$, NHCH$_3$ or N(CH$_3$)$_2$;

R$^{11}$ is (CH$_2$)$_{2-4}$NR$^9$R$^{9A}$;

R$^{12}$ is alkyl of 1–5 carbon atoms optionally substituted with one or more of F, Cl and Br;

W, Y and Z are independently H, F, Cl, Br, alkyl of 1–5 carbon atoms, NO$_2$, alkoxy of 1–5 carbon atoms, alkylthio of 1–5carbon atoms, OH, CF$_3$ or NH$_2$;

m is 0 or 1;

n is 0 or 1; and q is 0, 1 or 2; or a pharmaceutically suitable salt thereof;
with the following provisos:
1) R$^5$, R$^6$ and R$^7$ cannot all be H;
2) when R$^4$ is CO$_2$CH$_2$CH$_2$N(CH$_3$)$_2$, R$^6$ is CH$_2$CH$_3$, or R$^7$ is Cl, R$^1$ cannot be cyclohexyl;
3) when R$^1$ is cyclohexyl and R$^3$ is H, R$^6$ must be Cl or F, but R$^6$ and R$^8$ cannot both be Cl; and
4) when R$^6$ is CH$_3$, R$^7$ cannot be Cl.

Also provided is a method of inhibiting the growth of mammalian tumors by administering to a mammal a tumor-inhibiting amount of a compound described above.

Additionally provided are novel antitumor active phenylquinoline carboxylic acids and derivatives having the formula:

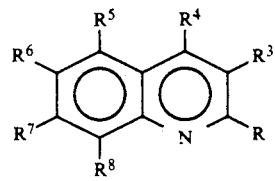

wherein

R is 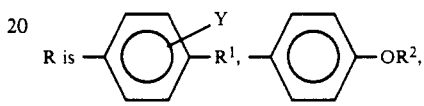

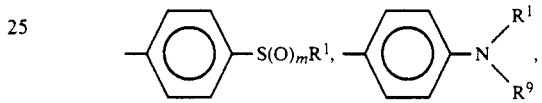

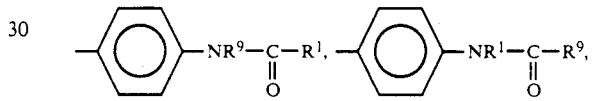

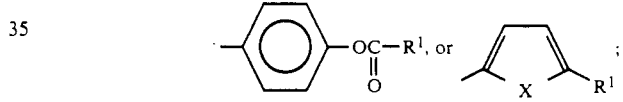

X is O, S(O)$_q$, NH or CH=N;

R$^1$ is CH$_3$CH$_2$(CH$_3$)CH, alkyl of 5–12 carbon atoms, alkenyl of 5–12 carbon atoms, cycloalkyl of 3–7 carbon atoms, cycloalkylalkyl of 5–12 carbon atoms,

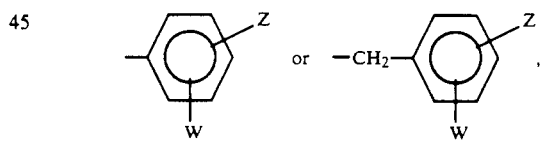

when R is

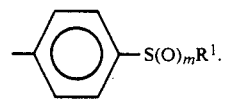

R$^1$ can be in addition alkyl of 3–4 carbon atoms;
R$^2$ is

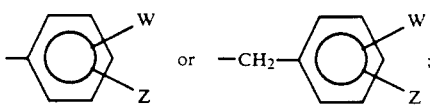

R$^3$ is H, alkoxy of 1–3 carbon atoms, alkylthio of 1–3 carbon atoms or alkyl of 1–2 carbon atoms optionally substituted with one or more of F, Cl, Br or $(CH_2)_pCOR^{10}$ where p is 1, 2, 3 or 4;

$R^4$ is $CO_2H$ or $CO_2R^{11}$;

$R^5$, $R^6$, $R^7$ and $R^8$ are independently H, F, Cl, Br, I, $CH_3$, $CF_3$, $S(O)_nR^{12}$ or $CH_2CH_3$, at least two of $R^5$, $R^6$, $R^7$, and $R^8$ being H;

$R^9$ and $R^{9A}$ are independently H or alkyl of 1 to 3 carbon atoms;

$R^{10}$ is OH, $OCH_3$, $OCH_2CH_3$, $NH_2$, $NHCH_3$ or $N(CH_3)_2$;

$R^{11}$ is $(CH_2)_{2-4}NR^9R^{9A}$;

$R^{12}$ is alkyl of 1-5 carbon atoms optionally substituted with one or more of F, Cl and Br;

W, Y and Z are independently H, F, Cl, Br, alkyl of 1-5 carbon atoms, $NO_2$, alkoxy of 1-5 carbon atoms, alkylthio of 1-5 carbon atoms, OH, $CF_3$ or $NH_2$;

m is 0 or 1;

n is 0 or 1; and q is 0, 1 or 2; or a pharmaceutically suitable salt thereof;

with the following provisos:

1) when $R^4$ is $CO_2H$, $R^1$ is phenyl or phenoxy, and $R^5$, $R^7$ and $R^8$ are H, $R^6$ cannot be Br;

2) $R^5$, $R^6$ and $R^7$ cannot all be H;

3) when $R^4$ is $CO_2CH_2CH_2N(CH_3)_2$, $R^6$ is $CH_2CH_3$, or $R^7$ is Cl, $R^1$ cannot be cyclohexyl;

4) when $R^1$ is cyclohexyl and $R^3$ is H, $R^6$ must be Cl or F, but $R^6$ and $R^8$ cannot both be Cl;

5) when $R^1$ is $4-H_2NC_6H_4$ and $R^3$ is H, $R^6$ cannot be Cl and $R^8$ cannot be Br; and 6) when $R^6$ is $CH_3$, $R^7$ cannot be Cl.

PREFERRED EMBODIMENTS

Preferred antitumor compounds have the formula:

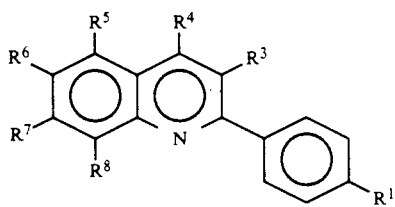

(II)

wherein $R^1$ is cycloalkyl of 3-7 carbon atoms; phenyl; phenyl substituted with one halogen, alkyl of 1-5 carbon atoms or $CF_3$; phenoxy; or phenoxy substituted with one halogen or alkyl of 1-5 carbon atoms;

$R^3$ is H or alkyl of 1-2 carbon atoms;

$R^4$ is $CO_2H$, a sodium or potassium salt thereof, or $CO_2R^{11}$;

$R^5$ and $R^6$ are independently H, halogen, $CH_3$ or $CF_3$; and $R^7$ and $R^8$ are independently H or halogen;

or a pharmaceutically suitable salt thereof;

with the provisos that:

1) $R^5$, $R^6$ and $R^7$ cannot all be H;

2) when $R^1$ is cyclohexyl and $R^3$ is H, $R^6$ must be Cl or F, but $R^6$ and $R^8$ cannot both be Cl; and 3) when $R^6$ is $CH_3$, then $R^7$ cannot be Cl.

More preferred antitumor compounds are compounds which have the formula:

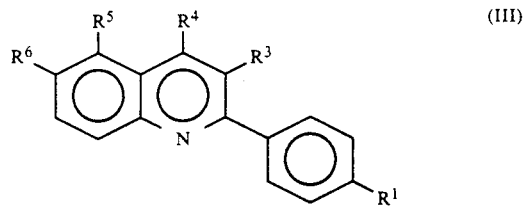

(III)

wherein $R^1$ is cyclohexyl, phenyl, phenyl substituted with halogen, phenoxy or phenoxy substituted with halogen;

$R^3$ is H or alkyl of 1-2 carbon atoms;

$R^4$ is $CO_2H$, a sodium or potassium salt thereof, or $CO_2R^{11}$;

$R^5$ or $R^6$ are independently H, halogen or $CF_3$, provided that both $R_5$ and $R_6$ are not H;

$R^{11}$ is $(CH_2)_{2-4}NR^9R^{9A}$; and $R^9$ and $R^{9A}$ are independently alkyl of 1 to 3 carbon atoms.

Especially preferred are the compounds of Formula III in which:

$R^1$ is phenyl, phenyl substituted with halogen, phenoxy, or phenoxy substituted with halogen;

$R^3$ is methyl;

$R^5$ is H or Cl;

$R^6$ is F or Cl; and $R^9$ and $R^{9A}$ are methyl.

Specifically preferred for their antitumor activity are:

(1) 2-(1,1'-Biphenyl-4-yl)-6-fluoro-3-methyl-4-quinolinecarboxylic acid, sodium or potassium salt.

(2) 6-Fluoro-3-methyl-2-(4-phenoxyphenyl)-4-quinolinecarboxylic acid, sodium or potassium salt.

(3) 2-(4'-Bromo-1,1'-biphenyl-4-yl)-6-fluoro-3-methyl4-quinolinecarboxylic acid, sodium or potassium salt.

(4) 2-(2'-Fluoro-1,1'-biphenyl-4yl)-6-fluoro-3-methyl-4-quinolinecarboxylic acid, sodium or potassium salt.

(5) 2-(1,1'-Biphenyl-4-yl)-5-chloro-6-fluoro-3-methyl4-quinolinecarboxylic acid, sodium or potassium salt.

(6) 6-Fluoro-2-(2'-fluoro-1,1'-biphenyl-4-yl)-3methyl-[(2-dimethylamino)ethyl]ester-4-quinolinecarboxylic acid, hydrochloride salt.

SYNTHESIS

The compounds useful in this invention (Formulae I, II and III) are prepared generally by condensation of an appropriately substituted isatin IV and a ketone V in what is known as the Pfitzinger reaction [Buu-Hoi, N. P.; Royer, R.; Xuong, N. D.; Jucquignon, P.; [J. Org. Chem., 18, 1209 (1953)] to give Ia; then, if desired, further conversion of functional groups on the quinoline provides further compounds of Formula I (Scheme 1). Isatins IV are prepared by the methods described by Papp and references given therein [Papp, F. D.; Adv. Heterocyclic Chem., 18, 1 (1975)]. The ketones V are prepared by Friedel-Crafts acylation as discussed by House [House, H. O.; Modern Synthetic Reactions, 2nd Ed., W. A. Benjamin, 1972, pp. 734ff].

In the following schemes, quinolines bearing up to two unspecified substituents $X^1$ and $X^2$ are depicted. The synthetic disclosure is general for quinolines, including all those within the scope of this invention. When certain values of $R^5$, $R^6$, $R^7$ and $R^8$ are desired, as will be apparent to one skilled in the art, a protected form of the functional group will be carried through the synthesis, to be deprotected to the desired functional group at a later stage.

Scheme 1

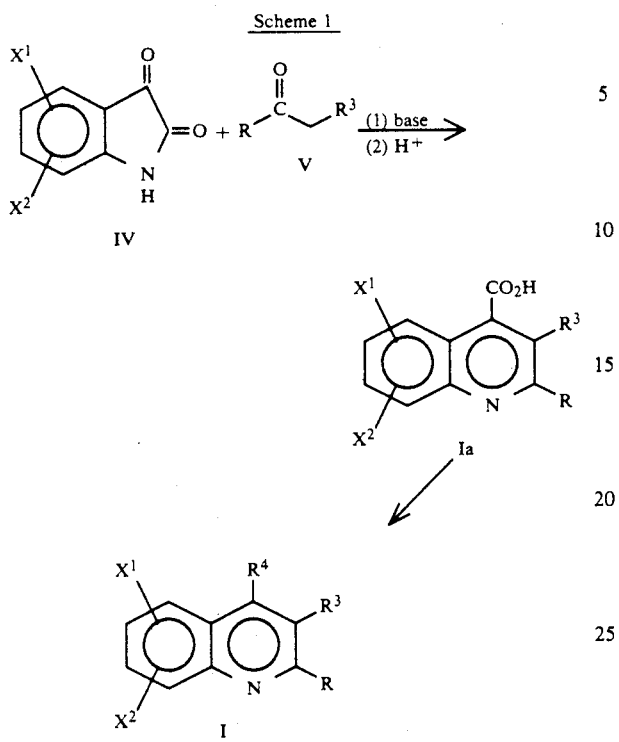

Compounds where $R^4$ is $CO_2H$ are prepared by reacting the appropriate substituted isatin (IV) with a substituted ketone (V) in a solvent such as ethanol with an aqueous solution of a base such as sodium hydroxide, $NH_4OH$ or potassium hydroxide at a temperature in the range of about 25° C. to the boiling point of the solvent used. Acidification of the reaction mixture with a mineral acid such as HCl or an organic acid such as acetic acid provides the quinoline carboxylic acid Ia. Compounds in which R is

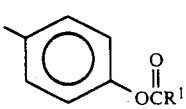

are prepared by acylation of the corresponding hydroxy compound with a carboxylic acid halide such as benzoyl chloride in an inert solvent such as chloroform or a hydrocarbon solvent (benzene) at a temperature in the range of about 0° C. to the boiling point of the solvent used, optionally in the presence of a base such as pyridine.

The aforementioned hydroxy compound is prepared from an ether by a dealkylation reaction using $BBr_3$ or $(CH_3)_3SiI$ in an inert solvent such as dimethylformamide, methylene chloride, or chloroform at a temperature in the range of about 0° C. to the boiling point of the solvent used (Scheme 2).

Scheme 2

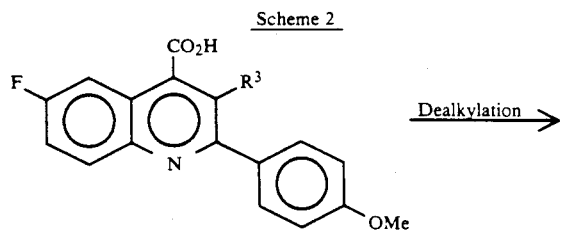

-continued

Scheme 2

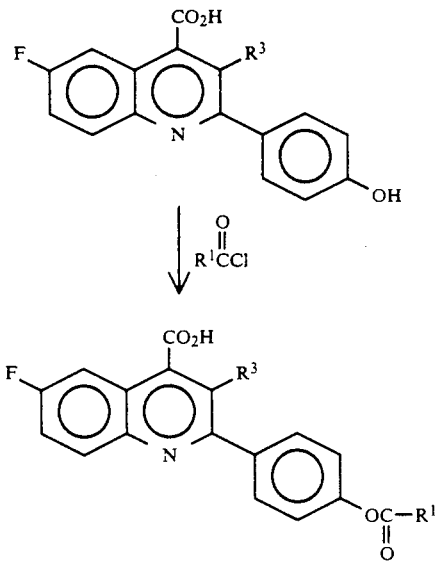

In Scheme 3, quinolines bearing up to two unspecified substituents $X^1$ and $X^2$ are depicted. The synthetic disclosure is general for quinolines, including all those within the scope of this invention. This method is preferred over the Pfitzinger procedure for certain substituents on the isatin (IV) such as $X^1=4$-Cl, or when W, Y or Z are $NO_2$, or when R is

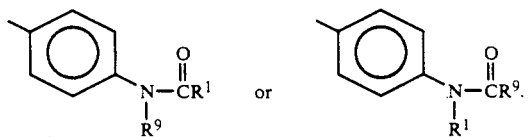

Scheme 3

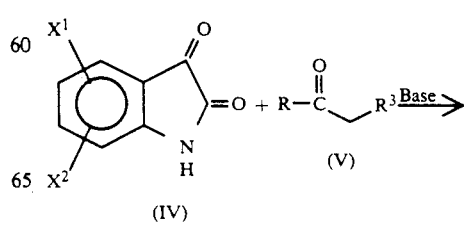

Scheme 3
-continued

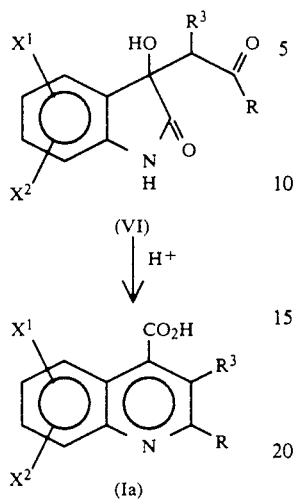

The compounds Ia of Scheme 3 are prepared by reacting the appropriate substituted isatin (IV) with a substituted Ketone (V) in a solvent such as ethanol with a base such as diethylamine or triethylamine at a temperature of 25° to 50° C. for 2 to 48 hours. Recrystallization of the product (VI) from a solvent is possible although decomposition often occurs. The product (VI) is dissolved in an appropriate solvent such as tetrahydrofuran containing 25–50% by volume of a mineral acid such as hydrochloric acid and heated to a temperature of 50° C. to the reflux temperature of the mixture for 2 to 48 hours to provide the quinoline carboxylic acid (Ia).

Quinolinecarboxylic acids such as (VIII) where $R^6$ is $R^{12}S(O)_n$ are best prepared by reacting the appropriately substituted quinolinecarboxylic acid (VII) where $R^6$ is F with an appropriate thiolate $R^{12}S-$ such as MeSK in a solvent such as dimethylformamide at a temperature of 50° C. to the reflux temperature of the solvent for 2 to 8 hours (Scheme 4).

It may be necessary, depending upon the reaction conditions chosen, to alkylate the thiol (IX) generated during the reaction by reacting the crude reaction product in an appropriate solvent such as acetone with an alkyl halide $R^{12}X$ such as methyl iodide with or without a base such as potassium carbonate at a temperature of 25° C. to the reflux temperature of the solvent for 2 to 24 hours. This gives the corresponding ester (X) which is hydrolyzed by reacting in an appropriate solvent such as ethanol with water and a base such as potassium hydroxide at reflux for 12 to 24 hours to give, after acidification of the reaction mixture with a mineral acid such as HCl, the quinolinecarboxylic acid (VIII). (VIII) can be converted to the corresponding sulfoxide by reacting (VIII) in an appropriate solvent such as ethyl acetate with an oxidizing reagent such as m-chloroperoxybenzoic acid at −20° to 25° C. for 6 to 24 hours.

Scheme 4

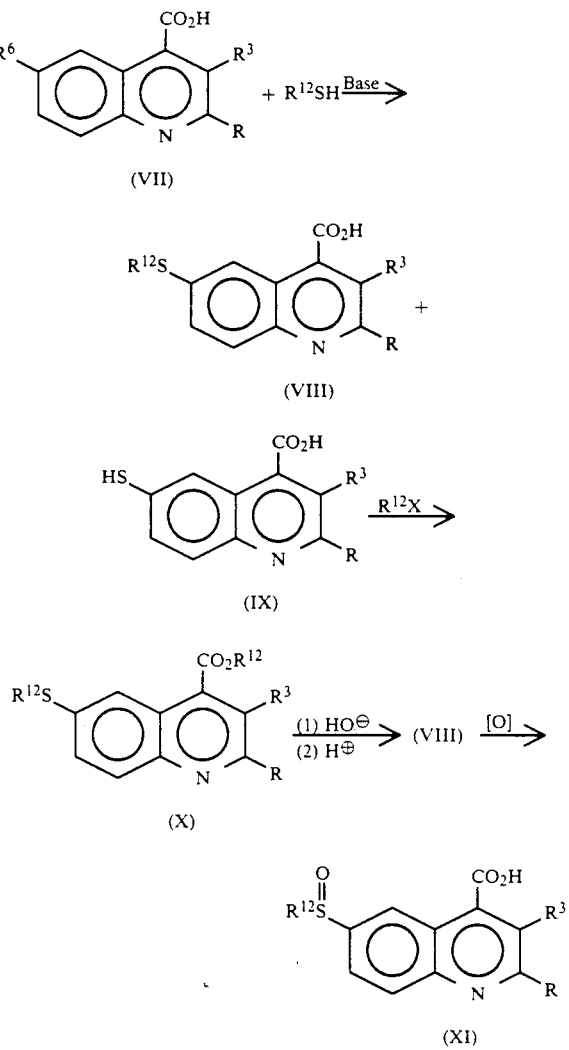

A salt of the carboxylic acid is prepared by dissolving the acid in a protic solvent such as ethanol, and then treating with a metal oxide or hydroxide such as sodium or potassium oxide or hydroxide or an amine such as 1-amino-2-butanol or lysine at a temperature in the range of about 0° C. to the boiling point of the solvent used. A salt of an amino group is prepared by dissolving the amine in a solvent such as ethyl ether and adding a mineral acid such as HCl.

A metal salt of a compound of Formula I (e.g., $R^4=CO_2Na$) can be converted to a corresponding ester in two steps. Conversion of the salt to an acid halide is carried out first by treatment with a reagent such as $SOCl_2$ or oxalyl chloride in an inert solvent such as a hydrocarbon (benzene) at a temperature in the range of about 25° C. to the boiling point of the solvent used. This reaction is followed by the addition of an alcohol, $R^{11}OH$, in a solvent such as tetrahydrofuran at a temperature in the range of 10° C. to the boiling point of the solvent used, optionally in the presence of a base such as pyridine, triethylamine, or 4-dimethylaminopyridine to provide the ester (Scheme 5).

Scheme 5

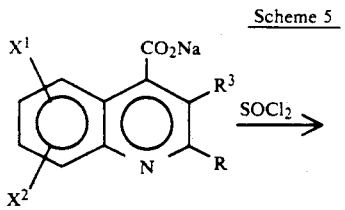

The invention can be further understood by the following examples in which parts and percentages are by weight unless otherwise indicated; all temperatures are in degrees Centigrade.

EXAMPLE 1

2-(4-Cyclohexylphenyl)-6-fluoro-3-methylquinoline-4-carboxylic acid

5-Fluoroisatin (100 g, 0.61 mole) and 4-cyclohexylpropiophenone (131 g, 0.61 mole) were suspended in 1100 ml of ethanol and stirred mechanically as a solution of 219 g (5.5 mole) of KOH in 550 ml of water was added dropwise. After the addition was complete, the mixture was heated at reflux for 12 hours, cooled, and the ethanol evaporated under reduced pressure. The resulting solid was dissolved in water and washed with ethyl ether. The aqueous layer was acidified with HCl. The resulting precipitate was filtered and dried. Recrystallization from dimethylformamide and water gave 117 g of 2-(4-cyclohexylphenyl)-6-fluoro3-methylquinoline-4-carboxylic acid, m.p. 316°–323°.

EXAMPLE 2

2-(4-Biphenylyl)-6-fluoro-3-methylquinoline-4-carboxylic acid

4-Phenylpropiophenone (18.9 g, 0.09 mole) and 5-fluoroisatin (20 g, 0.09 mole) were suspended in 360 ml of ethanol and stirred mechanically as a solution of 35.2 g KOH in 100 ml water was added dropwise over 15 minutes. The reaction mixture was heated at reflux for 12 hours, cooled, and the ethanol evaporated under reduced pressure. The resulting yellow solid was dissolved in water and washed with ethyl ether. The aqueous layer was cooled to 5° and acidified with glacial acetic acid. The resulting yellow precipitate was filtered and dried. Recrystallization from 200 ml of dimethylformamide and 25 ml water provided 13.8 g of 2-(4-biphenylyl)-6-fluoro-3-methylquinoline-4-carboxylic acid as a white solid, m.p. 303°–306° (d).

EXAMPLE 28

2-(2'-Fluoro-1,1'-biphenyl-4-yl)-6-fluoro-3-methyl4-quinolinecarboxylic acid

5-Fluoroisatin (72.6 g, 0.44 mole) and 4-(2-fluorophenyl) propiophenone (100 g, 0.44 mole) were suspended in 720 ml of ethanol and stirred mechanically as a solution of KOH (147.8 g, 2.64 mole) in 300 ml of water was added dropwise over 15 minutes. The reaction mixture was heated at reflux for 12 hours, cooled and the ethanol evaporated under reduced pressure. The resulting solid was dissolved in water and washed with ethyl ether. The aqueous layer was cooled to 5° and acidified with glacial acetic acid. The resulting precipitate was filtered, washed 2 times with 300 ml of ethyl ether and dried. Recrystallization from dimethylformamide and water gave 84 g of a white 2-(2'-Fluoro-1,1'-biphenyl-4-yl)-6-fluoro-3-methyl-4-quinolinecarboxylic acid, m.p. 315°–317°.

The compounds of Examples 1, 2 and 28, other compounds which have been prepared using the procedures described for the compounds of Examples 1, 2 and 28, and other compounds which may be prepared by such procedures, are listed in Table 1.

TABLE 1

| Ex. | R | $R^3$ | $R^6$ | $R^7$ | $R^8$ | m.p. (°C.) |
|---|---|---|---|---|---|---|
| 1 | 4-c-$C_6H_{11}C_6H_4$ | $CH_3$ | F | H | H | 316–323 |
| 2 | 4-$C_6H_5C_6H_4$ | $CH_3$ | F | H | H | 303–306(d) |
| 3 | 4-c-$C_6H_{11}C_6H_4$ | $CH_3$ | Cl | H | H | 320–322(d) |
| 4 | 4-c-$C_6H_{11}C_6H_4$ | H | Cl | H | H | 264–265 |
| 5 | 4-c-$C_6H_{11}C_6H_4$ | H | F | H | H | 280–284 |
| 6 | 4-c-$C_6H_{11}C_6H_4$ | $CH_3$ | $CH_3$ | H | H | 308–312(d) |
| 7 | 4-n-$C_{10}H_{21}C_6H_4$ | $CH_3$ | F | H | H | 256–261 |
| 8 | 4-n-$C_6H_{13}C_6H_4$ | $CH_3$ | F | H | H | 278–285 |
| 9 | 4-$CH_3CH_2(CH_3)CHC_6H_4$ | $CH_3$ | F | H | H | 290–297 |
| 10 | 4-c-$C_6H_{11}C_6H_4$ | $CH_3CH_2$ | F | H | H | 295–297 |
| 11 | 4-$C_6H_5OC_6H_4$ | $CH_3$ | F | H | H | 318–320(d) |
| 12 | 4-(4-$BrC_6H_4$)$C_6H_4$ | $CH_3$ | F | H | H | 318–323(d) |
| 13 | 4-$(CH_3)_2CHSC_6H_4$ | $CH_3$ | F | H | H | 280–283 |
| 14 | 4-$C_6H_5C_6H_4$ | $CH_3$ | $CH_3$ | H | H | 327–329(d) |
| 15 | 4-c-$C_6H_{11}C_6H_4$ | $CH_3CH_2$ | $CH_3$ | H | H | 290(d) |
| 16 | 4-$C_6H_5CH_2OC_6H_4$ | $CH_3$ | F | H | H | 297–302 |
| 17 | 4-$CH_3CH_2(CH_3)CHC_6H_4$ | $CH_3CH_2$ | F | H | H | 286–291 |
| 18 | 4-$C_6H_5C_6H_4$ | $CH_3CH_2$ | F | H | H | 274–279(d) |

TABLE 1-continued

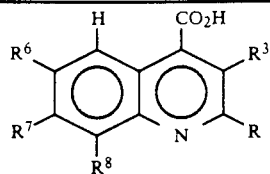

| Ex. | R | R³ | R⁶ | R⁷ | R⁸ | m.p. (°C.) |
|---|---|---|---|---|---|---|
| 19 | 4-$C_6H_5C_6H_4$ | $CH_3$ | Cl | H | H | 302–305 |
| 20 | 4-$C_6H_5OC_6H_4$ | $CH_3$ | Cl | H | H | 296–301 |
| 21 | 4-$C_6H_5SC_6H_4$ | $CH_3$ | Cl | H | H | 313–316 |
| 22 | 4-$C_6H_5CH_2C_6H_4$ | $CH_3$ | Cl | H | H | 265–275 |
| 23 | 4-(4-$FC_6H_4$)$C_6H_4$ | $CH_3$ | Cl | H | H | 319–323 |
| 24 | 4-(4-$CH_3OC_6H_4$)$C_6H_4$ | $CH_3$ | Cl | H | H | 310–314 |
| 25 | 4-$(CH_3)_2CHS(O)C_6H_4$ | $CH_3$ | F | H | H | |
| 26 | 4-$C_6H_5CH_2SC_6H_4$ | $CH_3$ | F | H | H | 281–287 |
| 27 | 4-(4-$BrC_6H_4$)$C_6H_4$ | $CH_3$ | Cl | H | H | 319–324(d) |
| 28 | 4-(2-$FC_6H_4$)$C_6H_4$ | $CH_3$ | F | H | H | 315–317 |
| 29 | 4-(4-$ClC_6H_4O$)$C_6H_4$ | $CH_3$ | F | H | H | 299–303 |
| 30 | 4-(4-$CH_3C_6H_4$)$C_6H_4$ | $CH_3$ | F | H | H | 317–319 |
| 31 | 4-(4-$FC_6H_4$)$C_6H_4$ | $CH_3$ | F | H | H | 310–314 |
| 32 | 4-(4-$CF_3C_6H_4$)$C_6H_4$ | $CH_3O$ | F | H | H | |
| 33 | 4-$C_6H_5C_6H_4$ | H | F | H | H | 272–278 |
| 34 | 4-$C_6H_5S(O)C_6H_4$ | $CH_3$ | F | H | H | 239–247 |
| 35 | 4-(4-$FC_6H_4O$)$C_6H_4$ | $CH_3$ | F | H | H | 291–297 |
| 36 | 4-(3,4-$Cl_2C_6H_3$)$C_6H_4$ | $CH_3$ | F | H | H | 315–319 |
| 37 | 4-$C_6H_5C_6H_4$ | $CH_3O$ | F | H | H | 219–223 |
| 38 | 4-(3-Cl,4-$CH_3C_6H_3$)$C_6H_4$ | $CH_3$ | F | H | H | 316–324 |
| 39 | 4-(3,4-$(CH_3)_2C_6H_3$)$C_6H_4$ | $CH_3$ | F | H | H | 321–324 |
| 40 | 4-(4-$(CH_3CH_2)C_6H_4$)$C_6H_4$ | $CH_3$ | F | H | H | 309–315 |
| 41 | 4-(3-$(CH_3CH_2)C_6H_4$)$C_6H_4$ | $CH_3$ | F | H | H | 252–260 |
| 42 | 4-$C_6H_5$-3-pyridyl | $CH_3$ | F | H | H | |
| 43 | 4-$C_6H_5$-2-furanyl | $CH_3$ | F | H | H | |
| 44 | 4-$C_6H_5$-2-thienyl | $CH_3$ | F | H | H | 345–350 |
| 45 | 4-c-$C_6H_{11}C_6H_4$ | $CH_3$ | Br | H | H | 325–330 |
| 46 | 4-c-$C_6H_{11}C_6H_4$ | $CH_3$ | Br | H | Br | 275–280 |
| 47 | 4-$C_6H_5C_6H_4$ | $CH_3$ | Cl | Cl | H | |
| 48 | 4-c-$C_6H_{11}C_6H_4$ | $CH_3$ | $CF_3$ | H | H | 320–325 |
| 49 | 4-$C_6H_5C_6H_4$ | $CH_3$ | H | Cl | H | 315–320 |
| 50 | 4-($C_6H_5O$)$C_6H_4$ | $CH_3$ | H | Cl | H | 315–318 |
| 51 | 4-$C_6H_5C_6H_4$ | $CH_3$ | $CH_3CH_2$ | H | H | 295–300 |
| 52 | 4-$C_6H_5C_6H_4$ | $CH_3$ | Br | H | H | 313–314 |
| 53 | 4-($C_6H_5O$)$C_6H_4$ | $CH_3$ | Br | H | H | 273–278 |
| 54 | 4-(4-$FC_6H_4$)$C_6H_4$ | $CH_3$ | F | Cl | H | |
| 55 | 4-$C_6H_5C_6H_4$ | $CH_3$ | H | $CH_3$ | H | 324–328 |
| 56 | 4-$C_6H_5C_6H_4$ | $CH_3$ | $CF_3$ | H | H | 320–323 |
| 57 | 4-($C_6H_5O$)$C_6H_4$ | $CH_3$ | $CF_3$ | H | H | 294–298 |
| 58 | 4-$C_6H_5C_6H_4$ | $CH_3$ | $CH_3$ | H | H | 333–336 |
| 59 | 4-($C_6H_5O$)$C_6H_4$ | $CH_3$ | $CH_3$ | Cl | H | 314–318 |
| 60 | 4-$C_6H_5C_6H_4$ | $CH_3$ | Br | H | Br | 270–273 |
| 61 | 4-$C_6H_5C_6H_4$ | $CH_3$ | F | Cl | H | 327–332 |
| 62 | 4-c-$C_3H_5C_6H_4$ | $CH_3$ | F | H | H | |
| 63 | 4-c-$C_5H_9C_6H_4$ | $CH_3$ | F | H | H | |
| 64 | 4-($C_6H_5(CH_3)N$)$C_6H_4$ | $CH_3$ | F | H | H | |
| 65 | 4-($C_6H_5CONH$)$C_6H_4$ | $CH_3$ | F | H | H | |
| 66 | 4-($C_6H_5CO_2$)$C_6H_4$ | $CH_3$ | F | H | H | |
| 67 | 5-$C_6H_5$-2-imidazoyl | $CH_3$ | F | H | H | |
| 68 | (4-$C_6H_5$,2-$CH_3$)$C_6H_3$ | $CH_3$ | F | H | H | 316–320 |
| 69 | 4-(2-$FC_6H_4$), 3-$FC_6H_3$ | $CH_3$ | F | H | H | |
| 70 | 4-(2-$FC_6H_4$)$C_6H_4$ | $CH_3$ | Cl | H | H | 314–330 |
| 71 | 4-$C_6H_5C_6H_4$ | $CH_3$ | I | H | H | 325–327 |
| 72 | 4-(4-$CF_3C_6H_4$)$C_6H_4$ | $CH_3$ | F | H | H | 326–328 |
| 73 | 4-(3-$FC_6H_4$)$C_6H_4$ | $CH_3$ | F | H | H | 305–310 |
| 74 | 4-(2,4-$F_2C_6H_3$)$C_6H_4$ | $CH_3$ | F | H | H | 325–328 |
| 75 | 4-(4-$FC_6H_4O$)$C_6H_4$ | H | F | H | H | 310–315 |
| 207 | (4-$C_6H_5$, 3-F)$C_6H_3$ | $CH_3$ | F | H | H | 314–316(d) |
| 208 | (4-$C_6H_5$, 2-F)$C_6H_3$ | $CH_3$ | F | H | H | 306–309(d) | c-$C_6H_{11}$ = cyclohexyl
c-$C_5H_9$ = cyclopentyl
c-$C_3H_5$ = cyclopropyl

EXAMPLE 76

2-(4-Biphenyl)-3-methyl-6-methylthio-4-quinoline carboxylic acid.

The compound of Example 2, 2-(4-biphenyl)-6-fluoro-3-methyl-4-quinolinecarboxylic acid, (7.2 g, 0.02 mole) and potassium methylmercaptide (6 g) were dissolved in 100 ml of dimethylformamide and warmed at 130° for 3 hours. The mixture was cooled and the solvent evaporated under reduced pressure. The residue was dissolved in 250 ml of $H_2O$, filtered and the filtrate acidified to pH 2. The yellow precipitate was filtered and dried. A portion of the yellow precipitate (1.8 g, 0.005 mole) was suspended in acetone containing 5 ml of methyl iodide and 4 g of potassium carbonate and was heated to reflux for 24 hours. The reaction mixture was filtered and evaporated at reduced pressure. The residue was dissolved in ethyl ether, washed with H₂O, dried with sodium sulfate and evaporated at reduced pressure to give a solid. The solid obtained in this manner from several batches (6 g) was combined and dissolved in 70 ml of ethanol and 30 ml of H₂O containing 10g of potassium hydroxide. The mixture was heated at reflux for 12 hours. The mixture was cooled, evaporated at reduced pressure, dissolved in 300 ml of H₂O and washed with ethyl ether. The aqueous solution was acidified to pH 2 with HCl and the precipitate collected, washed with water and hot ethanol to give 4.9 g of 2-(4-Biphenyl)3-methyl-6-methylthio-4-quinolinecarboxylic acid, m.p. 316°–318° (d).

The compound of Example 76 and other compounds which can be prepared using this procedure are listed in Table 2.

TABLE 2

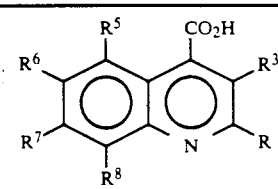

| Ex. | R | $R^3$ | $R^5$ | $R^6$ | $R^7$ | $R^8$ | m.p. (°C.) |
|---|---|---|---|---|---|---|---|
| 76 | 4-$C_6H_5C_6H_4$ | $CH_3$ | H | $CH_3S$ | H | H | 316–318(d) |
| 77 | 4-$C_6H_5C_6H_4$ | $CH_3$ | H | $CH_3S(O)$ | H | H | |
| 78 | 4-(2-$FC_6H_4)C_6H_4$ | $CH_3$ | H | $CH_3S$ | H | H | |
| 79 | 4-(4-$CH_3C_6H_4)C_6H_4$ | $CH_3$ | H | $CH_3S$ | H | H | |

EXAMPLE 81

2-(4-Biphenyl)-5-chloro-6-fluoro-3-methyl-4-quinolinecarboxylic acid

4-Chloro-5-fluoroisatin (4 g, 0.02 mole), diethylamine (1.46 g, 0.02 mole) and 4-phenylpropiophenone (4.4 g, 0.021 mole) were suspended in 100 ml of ethanol and stirred for 12 hours. The precipitate was filtered, washed with cold ethanol and dried to give 2.1 g of crude adduct (m.p. 202°–206°).

This was dissolved in 75 ml of tetrahydrofuran and 30 ml of concentrated HCl. The resulting solution was refluxed for 24 hours, cooled and diluted with H₂O. The tetrahydrofuran was evaporated under reduced pressure. The precipitate was filtered, washed with ether and boiled with methanol to give 0.90 g of 2-(4-biphenyl)-5-chloro-6-fluoro-3-methyl-4-quinolinecarboxylic acid as a crystalline solid, m.p. 300°–305°.

EXAMPLE 86

6-Fluoro-3-methyl-2-(4-nitrophenoxyphenyl)-4-quinolinecarboxylic acid

5-Fluoroisatin (2.0 g, 0.0104 mole), diethylamine (0.77 g, 0.0105 mole) and 4-(4-nitrophenoxy)propiophenone (2.82 g, 0.0104 mole) were suspended in 100 ml of ethanol and stirred at 25° for 12 hours. The precipitate was filtered, washed with toluene and air dried to give 3.0 g crude adduct.

The crude product obtained from two of the above preparations (5.0 g, 0.0108 mole) was combined in 180 ml of tetrahydrofuran and 40 ml of concentrated HCl. The resulting solution was refluxed for 12 hours, cooled and the solvent was evaporated under reduced pressure. The solid residue was washed with ethyl ether and dried to give 4.37 g of 6-fluoro-3-methyl2-(4-nitrophenoxyphenyl)-4-quinolinecarboxylic acid as a white solid, m.p. 335°–337°.

The compounds of Examples 81 and 86, other compounds which have been prepared using the procedures for the compounds of Examples 81 and 86, and other compounds which may be prepared by such procedures, are listed in Table 3.

TABLE 3

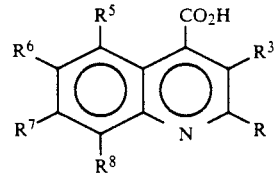

| Ex. | R | $R^3$ | $R^5$ | $R^6$ | $R^7$ | $R^8$ | m.p. (°C.) |
|---|---|---|---|---|---|---|---|
| 80 | 4-$C_6H_5C_6H_4$ | $CH_3$ | Cl | H | H | H | 295–296(d) |
| 81 | 4-$C_6H_5C_6H_4$ | $CH_3$ | Cl | F | H | H | 305–308(d) |
| 82 | 4-$C_6H_5C_6H_4$ | $CH_3$ | Cl | H | Cl | H | 301–305(d) |
| 83 | 4-$C_6H_5C_6H_4$ | $CH_3$ | Cl | $CH_3$ | H | H | 295–298(d) |
| 84 | 4-(2-$FC_6H_4)C_6H_4$ | $CH_3$ | Cl | F | H | H | 300–305 |
| 85 | 4-(4-$CH_3C_6H_4)C_6H_4$ | $CH_3$ | Cl | F | H | H | 293–296 |
| 86 | 4-(4-$NO_2C_6H_4O)C_6H_4$ | $CH_3$ | H | F | H | H | 335–337 |
| 87 | 4-$C_6H_5C_6H_4$ | $CH_3$ | H | H | F | H | 307–311(d) |
| 88 | 4-(4-$CF_3C_6H_4)C_6H_4$ | $CH_3CH_2$ | Cl | F | H | H | |
| 89 | 4-(3-Cl, 4-$CH_3C_6H_3)C_6H_4$ | $CH_3$ | Cl | F | H | H | |
| 90 | 4-(3-Cl, 4-$CH_3C_6H_3)C_6H_4$ | $CH_3$ | H | H | H | H | |

EXAMPLE 91

Sodium 2-(4-Cyclohexylphenyl)-6-fluoro-3-methylquinoline-4-carboxylate

The compound of Example 1 (10.0 g, 0.0275 mole) was suspended in 400 ml of ethanol and treated with 1N NaOH (27.5 ml, 0.0275 mole). The mixture was stirred until the solution was clear; the ethanol and water were evaporated at reduced pressure to give 9.95 g of the sodium salt as a white solid, m.p. 350°(d).

EXAMPLE 92

Sodium 2-(4-Biphenylyl)-6-fluoro-3-methylquinoline4-carboxylate

The compound of Example 2 (3.57 g, 0.01 mole) was dissolved in 500 ml of ethanol, treated with 1N NaOH (10 ml), and heated at reflux for 30 minutes. The ethanol and water were evaporated at reduced pressure to provide 3.6 g of the sodium salt as a pale tan solid, m.p. >360°.

EXAMPLE 118

Sodium 2-(2'-Fluoro-1,1'-biphenyl-4-yl)-6-fluoro-3-methyl-quinoline-4-carboxylate The compound of Example 28 (37.5 g, 0.10 mole) was suspended in 1,000 ml of ethanol and treated with 1N NaOH (100 ml, 0.10 mole). The mixture was warmed and stirred until clear; the ethanol and water were evaporated at reduced pressure to give 39.6 g of the white solid sodium 2-(2'-fluoro-1,1'-biphenyl-4-yl)-6-fluoro-3-methylquinoline-4-carboxylate, m.p. >360°.

EXAMPLE 164

Sodium 2-(4-Biphenylyl)-5-chloro-6-fluoro-3-methylquinoline-4-carboxylate

The compound of Example 81 (7.85 g, 0.02 mole) was suspended in 150 ml of water and treated with 1N NaOH (19.9 ml, 0.0199 mole), and 150 ml of ethanol was added. The mixture was stirred until the solution was clear and filtered to remove any insoluble material. The ethanol and water were removed at reduced pressure to give 8.1 g of the white solid sodium salt, m.p. >360°.

The compounds of Examples 91, 92, 118 and 164, other compounds which have been prepared by the procedures given above, and other compounds which can be prepared using such procedures are listed in Table 4.

TABLE 4

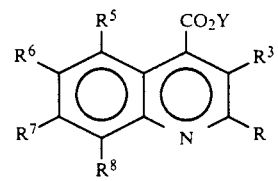

| Ex. | R | $R^3$ | $R^5$ | $R^6$ | $R^7$ | $R^8$ | Y | m.p. (°C.) |
|---|---|---|---|---|---|---|---|---|
| 91 | 4-c-$C_6H_{11}C_6H_4$ | $CH_3$ | H | F | H | H | Na | 350(d) |
| 92 | 4-$C_6H_5C_6H_4$ | $CH_3$ | H | F | H | H | Na | >360 |
| 93 | 4-c-$C_6H_{11}C_6H_4$ | $CH_3$ | H | Cl | H | H | Na | >350 |
| 94 | 4-c-$C_6H_{11}C_6H_4$ | H | H | Cl | H | H | Na | >350 |
| 95 | 4-c-$C_6H_{11}C_6H_4$ | H | H | F | H | H | Na | >350 |
| 96 | 4-c-$C_6H_{11}C_6H_4$ | $CH_3$ | H | $CH_3$ | H | H | Na | 342–351 |
| 97 | 4-n-$C_{10}H_{21}C_6H_4$ | $CH_3$ | H | F | H | H | Na | 332–335 |
| 98 | 4-n-$C_6H_{13}C_6H_4$ | $CH_3$ | H | F | H | H | Na | |
| 99 | 4-$CH_3CH_2(CH_3)CHC_6H_4$ | $CH_3$ | H | F | H | H | Na | 340–345 |
| 100 | 4-c-$C_6H_{11}C_6H_4$ | $CH_3CH_2$ | H | F | H | H | Na | >350 |
| 101 | 4-$C_6H_5OC_6H_4$ | $CH_3$ | H | F | H | H | Na | >350 |
| 102 | 4-(4-Br$C_6H_4$)$C_6H_4$ | $CH_3$ | H | F | H | H | Na | >350 |
| 103 | 4-$(CH_3)_2CHSC_6H_4$ | $CH_3$ | H | F | H | H | Na | 339–343 |
| 104 | 4-$C_6H_5C_6H_4$ | $CH_3$ | H | $CH_3$ | H | H | Na | >350 |
| 105 | 4-c-$C_6H_{11}C_6H_4$ | $CH_3CH_2$ | H | $CH_3$ | H | H | Na | >350 |
| 106 | 4-$C_6H_5CH_2OC_6H_4$ | $CH_3$ | H | F | H | H | Na | >350 |
| 107 | 4-$CH_3CH_2(CH_3)CHC_6H_4$ | $CH_3CH_2$ | H | F | H | H | Na | 302–306 |
| 108 | 4-$C_6H_5C_6H_4$ | $CH_3CH_2$ | H | F | H | H | Na | >350 |
| 109 | 4-$C_6H_5C_6H_4$ | $CH_3$ | H | Cl | H | H | Na | >350 |
| 110 | 4-$C_6H_5OC_6H_4$ | $CH_3$ | H | Cl | H | H | Na | 170–175 |
| 111 | 4-$C_6H_5SC_6H_4$ | $CH_3$ | H | Cl | H | H | Na | 319–324 |
| 112 | 4-$C_6H_5CH_2C_6H_4$ | $CH_3$ | H | Cl | H | H | Na | 305–315 |
| 113 | 4-(4-F$C_6H_4$)$C_6H_4$ | $CH_3$ | H | Cl | H | H | Na | >350 |
| 114 | 4-(4-$CH_3OC_6H_4$)$C_6H_4$ | $CH_3$ | H | Cl | H | H | Na | >360 |
| 115 | 4-$(CH_3)_2CHS(O)C_6H_4$ | $CH_3$ | H | F | H | H | Na | |
| 116 | 4-$C_6H_5CH_2SC_6H_4$ | $CH_3$ | H | F | H | H | Na | |
| 117 | 4-(4-Br$C_6H_4$)$C_6H_4$ | $CH_3$ | H | Cl | H | H | Na | >360 |
| 118 | 4-(2-F$C_6H_4$)$C_6H_4$ | $CH_3$ | H | F | H | H | Na | >360 |
| 119 | 4-(4-Cl$C_6H_4O$)$C_6H_4$ | $CH_3$ | H | F | H | H | Na | >350 |
| 120 | 4-(4-$CH_3C_6H_4$)$C_6H_4$ | $CH_3$ | H | F | H | H | Na | >350 |
| 121 | 4-(4-F$C_6H_4$)$C_6H_4$ | $CH_3$ | H | F | H | H | Na | >360 |
| 122 | 4-(4-$CF_3C_6H_4$)$C_6H_4$ | $CH_3O$ | H | F | H | H | Na | |
| 123 | 4-$C_6H_5C_6H_4$ | H | H | F | H | H | Na | >360 |
| 124 | 4-$C_6H_5S(O)C_6H_4$ | $CH_3$ | H | F | H | H | Na | 251–260 |
| 125 | 4-(4-F$C_6H_4O$)$C_6H_4$ | $CH_3$ | H | F | H | H | Na | 338–351 |
| 126 | 4-(3,4-$Cl_2C_6H_3$)$C_6H_4$ | $CH_3$ | H | F | H | H | Na | >360 |
| 127 | 4-$C_6H_5C_6H_4$ | $CH_3O$ | H | F | H | H | Na | 345–349 |
| 128 | 4-(3-Cl,4-$CH_3C_6H_3$)$C_6H_4$ | $CH_3$ | H | F | H | H | Na | >360 |
| 129 | 4-(3,4-$(CH_3)_2C_6H_3$)$C_6H_4$ | $CH_3$ | H | F | H | H | Na | >350 |
| 130 | 4-(4-$(CH_3CH_2)C_6H_4$)$C_6H_4$ | $CH_3$ | H | F | H | H | Na | >360 |
| 131 | 4-(3-$(CH_3CH_2)C_6H_4$)$C_6H_4$ | $CH_3$ | H | F | H | H | Na | |
| 132 | 4-$C_6H_5$-3-pyridyl | $CH_3$ | H | F | H | H | Na | |
| 133 | 4-$C_6H_5$-2-furanyl | $CH_3$ | H | F | H | H | Na | |
| 134 | 4-$C_6H_5$-2-thienyl | $CH_3$ | H | F | H | H | Na | >360 |
| 135 | 4-c-$C_6H_{11}C_6H_4$ | $CH_3$ | H | Br | H | H | Na | >360 |
| 136 | 4-c-$C_6H_{11}C_6H_4$ | $CH_3$ | H | Br | H | Br | Ha | 298–300(d) |

TABLE 4-continued

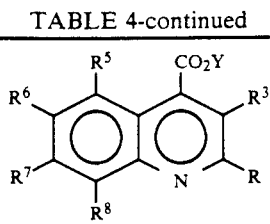

| Ex. | R | $R^3$ | $R^5$ | $R^6$ | $R^7$ | $R^8$ | Y | m.p. (°C.) |
|---|---|---|---|---|---|---|---|---|
| 137 | $4\text{-}C_6H_5C_6H_4$ | $CH_3$ | H | Cl | Cl | H | Na | |
| 138 | $4\text{-}\underline{c}\text{-}C_6H_{11}C_6H_4$ | $CH_3$ | H | $CF_3$ | H | H | Na | |
| 139 | $4\text{-}C_6H_5C_6H_4$ | $CH_3$ | H | H | Cl | H | Na | >360 |
| 140 | $4\text{-}(C_6H_5O)C_6H_4$ | $CH_3$ | H | H | Cl | H | Na | |
| 141 | $4\text{-}C_6H_5C_6H_4$ | $CH_3$ | H | $CH_3CH_2$ | H | H | Na | >360 |
| 142 | $4\text{-}C_6H_5C_6H_4$ | $CH_3$ | H | Br | H | H | Na | >360 |
| 143 | $4\text{-}(C_6H_5O)C_6H_4$ | $CH_3$ | H | Br | H | H | Na | 228 |
| 144 | $4\text{-}(4\text{-}FC_6H_4)C_6H_4$ | $CH_3$ | H | F | Cl | H | Na | |
| 145 | $4\text{-}C_6H_5C_6H_4$ | $CH_3$ | H | H | $CH_3$ | H | Na | >350 |
| 146 | $4\text{-}C_6H_5C_6H_4$ | $CH_3$ | H | $CF_3$ | H | H | Na | >360 |
| 147 | $4\text{-}(C_6H_5O)C_6H_4$ | $CH_3$ | H | $CF_3$ | H | H | Na | 338–342 |
| 148 | $4\text{-}C_6H_5C_6H_4$ | $CH_3$ | H | $CH_3$ | Cl | H | Na | >360 |
| 149 | $4\text{-}(C_6H_5O)C_6H_4$ | $CH_3$ | H | $CH_3$ | Cl | H | Na | 318–320 |
| 150 | $4\text{-}C_6H_5C_6H_4$ | $CH_3$ | H | Br | H | Br | Na | 340–345 |
| 151 | $4\text{-}C_6H_5C_6H_4$ | $CH_3$ | H | F | Cl | H | Na | >360 |
| 152 | $4\text{-}\underline{c}\text{-}C_3H_5C_6H_4$ | $CH_3$ | H | F | H | H | Na | |
| 153 | $4\text{-}\underline{c}\text{-}C_5H_9C_6H_4$ | $CH_3$ | H | F | H | H | Na | |
| 154 | $4\text{-}(C_6H_5(CH_3)N)C_6H_4$ | $CH_3$ | H | F | H | H | Na | |
| 155 | $4\text{-}(C_6H_5CONH)C_6H_4$ | $CH_3$ | H | F | H | H | Na | |
| 156 | $4\text{-}(C_6H_5CO_2)C_6H_4$ | $CH_3$ | H | F | H | H | Na | |
| 157 | $4\text{-}C_6H_5\text{-}2\text{-imidazoyl}$ | $CH_3$ | H | F | H | H | Na | |
| 158 | $4\text{-}C_6H_5,2\text{-}CH_3C_6H_3$ | $CH_3$ | H | F | H | H | Na | >360 |
| 159 | $4\text{-}(2\text{-}FC_6H_4),3\text{-}FC_6H_3$ | $CH_3$ | H | F | H | H | Na | |
| 160 | $4\text{-}(2\text{-}FC_6H_4)C_6H_4$ | $CH_3$ | H | Cl | H | H | Na | 176–177 |
| 161 | $4\text{-}C_6H_5C_6H_4$ | $CH_3$ | H | $CH_3S$ | H | H | Na | >350 |
| 162 | $4\text{-}C_6H_5C_6H_4$ | $CH_3$ | H | $CH_3S(O)$ | H | H | Na | |
| 163 | $4\text{-}C_6H_5C_6H_4$ | $CH_3$ | Cl | H | H | H | Na | >360 |
| 164 | $4\text{-}C_6H_5C_6H_4$ | $CH_3$ | Cl | F | H | H | Na | >360 |
| 165 | $4\text{-}C_6H_5C_6H_4$ | $CH_3$ | Cl | H | Cl | H | Na | >350 |
| 166 | $4\text{-}C_6H_5C_6H_4$ | $CH_3$ | Cl | $CH_3$ | H | H | Na | >340 |
| 167 | $4\text{-}(2\text{-}FC_6H_4)C_6H_4$ | $CH_3$ | Cl | F | H | H | Na | 330–335(d) |
| 168 | $4\text{-}(4\text{-}CH_3C_6H_4)C_6H_4$ | $CH_3$ | Cl | F | H | H | Na | >345 |
| 169 | $4\text{-}\underline{c}\text{-}C_6H_{11}C_6H_4$ | $CH_3$ | H | F | H | H | K | 350–360(d) |
| 170 | $4\text{-}C_6H_5C_6H_4$ | $CH_3$ | H | F | H | H | K | >350 |
| 171 | $4\text{-}C_6H_5C_6H_4$ | $CH_3$ | H | Cl | H | H | K | >350 |
| 172 | $4\text{-}(C_6H_5O)C_6H_4$ | $CH_3$ | H | Cl | H | H | K | 164–171 |
| 173 | $4\text{-}(C_6H_5S)C_6H_4$ | $CH_3$ | H | Cl | H | H | K | 310–325 |
| 174 | $4\text{-}(4\text{-}BrC_6H_4)C_6H_4$ | $CH_3$ | H | F | H | H | K | 370 |
| 175 | $4\text{-}(4\text{-}BrC_6H_4)C_6H_4$ | $CH_3$ | H | Cl | H | H | K | >360 |
| 176 | $4\text{-}(2\text{-}FC_6H_4)C_6H_4$ | $CH_3$ | H | F | H | H | K | 339–346 |
| 177 | $4\text{-}(4\text{-}FC_6H_4)C_6H_4$ | $CH_3$ | H | F | H | H | K | 270–275 |
| 178 | $4\text{-}C_6H_5C_6H_4$ | $CH_3$ | H | F | H | H | lysine | 222–231 |
| 179 | $4\text{-}C_6H_5C_6H_4$ | $CH_3$ | H | F | H | H | 1-amino-2-butanol | 128–134 |
| 180 | $4\text{-}\underline{n}\text{-}C_6H_{13}C_6H_4$ | $CH_3$ | H | F | H | H | lysine | 205–212 |
| 181 | $4\text{-}\underline{c}\text{-}C_6H_{11}C_6H_4$ | $CH_3$ | H | F | H | H | lysine | 226–231 |
| 182 | $4\text{-}C_6H_5C_6H_4$ | H | H | F | H | H | K | 326–329 |
| 183 | $4\text{-}(4\text{-}BrC_6H_4)C_6H_4$ | $CH_3$ | H | F | H | H | lysine | 253–258 |
| 184 | $4\text{-}(4\text{-}NO_2C_6H_4O)C_6H_4$ | $CH_3$ | H | F | H | H | Na | >360 |
| 185 | $4\text{-}C_6H_5C_6H_4$ | $CH_3$ | H | I | H | H | Na | >360 |
| 186 | $4\text{-}C_6H_5C_6H_4$ | $CH_3$ | H | H | F | H | Na | 360 |
| 187 | $4\text{-}(4\text{-}FC_6H_4O)C_6H_4$ | H | H | F | H | H | Na | |
| 188 | $4\text{-}(2,4\text{-}F_2C_6H_3)C_6H_4$ | $CH_3$ | H | F | H | H | Na | |
| 189 | $4\text{-}(2\text{-}FC_6H_4)C_6H_4$ | $CH_3$ | Cl | F | H | H | Na | 330–335(d) |
| 190 | $4\text{-}(3\text{-}FC_6H_4)C_6H_4$ | $CH_3$ | H | H | H | H | Na | >360 |
| 191 | $4\text{-}(4\text{-}HOC_6H_4)C_6H_4$ | $CH_3$ | H | F | H | H | Na | >360 |
| 209 | $4\text{-}(4\text{-}CF_3C_6H_4)C_6H_4$ | $CH_3$ | H | F | H | H | Na | >360 |
| 210 | $(4\text{-}C_6H_5, 3\text{-}F)C_6H_3$ | $CH_3$ | H | F | H | H | Na | >360 |
| 211 | $(4\text{-}C_6H_5, 2\text{-}F)C_6H_3$ | $CH_3$ | H | F | H | H | Na | 355–360 | lysine = $H_3\overset{+}{N}CH_2CH_2CH_2CH_2\underset{NH_2}{\overset{|}{C}H}CO_2H$ 1-amino-2-butanol = $H_3\overset{+}{N}CHCHCH_2CH_3$
$\phantom{H_3NCH}\underset{OH}{|}$

EXAMPLE 192

6-Chloro-2-(4'-hydroxy-1,1'biphenyl-4-yl)-3-methyl-4-quinolinecarboxylic acid

The compound of Example 24 (4.0 g, 0.01 mole) was added in portions to a solution of borontribromide (5.7 ml, 0.06 mole) in 90 ml of chloroform at 25° under nitrogen. This maroon suspension was stirred for 1 hour then poured onto wet ice. The resulting yellow precipitate was filtered, washed with chloroform and air dried. The solid was dissolved in 1N NaOH, washed with chloroform and then acidified with glacial acetic acid to give a yellow precipitate which was filtered and air dried to give 4.2 g of the yellow solid 6-chloro-2-(4'-hydroxy-1,1'-biphenyl-4-yl)-3-methyl-4-quinolinecarboxylic acid, m.p. >360°.

The compound of Example 192 and other compounds which can be prepared using such procedures are listed in Table 5.

TABLE 5

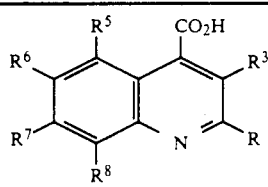

| Ex. | R | $R^3$ | $R^5$ | $R^6$ | $R^7$ | $R^8$ | m.p. (°C.) |
|---|---|---|---|---|---|---|---|
| 192 | 4-(4-HOC$_6$H$_4$)C$_6$H$_4$ | CH$_3$ | H | Cl | H | H | >360 |
| 193 | 4-(4-HOC$_6$H$_4$)C$_6$H$_4$ | CH$_3$ | H | F | H | H | |
| 194 | 4-(4-HOC$_6$H$_4$)C$_6$H$_4$ | CH$_3$ | Cl | F | H | H | |

EXAMPLE 197

6-Fluoro-2-(2'-fluoro-1,1'-biphenyl-4-yl)-3-methyl-[(2dimethylamino)ethyl]ester-4-quinolinecarboxylic acid The compound of Example 118 (20.00 g, 0.0504 moles) was suspended in a solution of 1000 ml of dry benzene, 1000 ml of dry THF and 20.0 ml (excess) of oxalyl chloride. This suspension was heated at reflux for 9 hours under nitrogen. The reaction was cooled, the precipitate was filtered and the resulting solution was evaporated to dryness under reduced pressure. The resulting solid was dissolved in a solution of 1000 ml of dry THF, 20.0 ml (excess) of N,N-dimethylethanolamine containing 0.01 g of dimethylaminopyridine. The resulting solution was refluxed for 12 hours under nitrogen. The reaction was cooled, the precipitate was filtered and the resulting solution was evaporated the dryness under reduced pressure. The resulting solid was chromatographed (silica gel:CH$_2$Cl$_2$:MeOH 0-5% gradient) to yield 17.88 g of the title compound, m.p. 146°-149° C.

EXAMPLE 198

[6-Fluoro-2-(2'-fluoro-1,1'-biphenyl-4-yl)3-methyl-[(2-dimethylamino)ethyl]ester-4-quinolinecarboxylic acid]hydrochloride The compound of Example 197 (18.66 g, 0.0417 mole) was dissolved in a solution of 50 ml of dry THF and 500 ml of dry ether. This solution was added slowly to 1000 ml of dry ether saturated with HCl gas. The resulting suspension was stirred for 30 minutes at 25° C. The reaction was then filtered, washed with ether and dried under a vacuum overnight and gave a yellow solid, 20.62 g of the title compound, m.p. 238° C. dec.

The compounds of Examples 197 and 198, other compounds which have been prepared by the procedures given above, and other compounds which can be prepared using such procedures are listed in Table 6.

TABLE 6

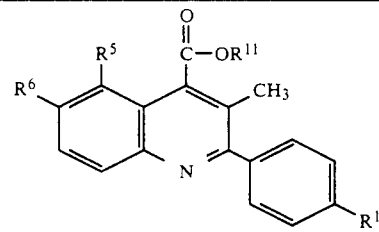

| Ex. | $R^1$ | $R^{11}$ | $R^5$ | $R^6$ | m.p. (°C.) |
|---|---|---|---|---|---|
| 195 | 4-C$_6$H$_5$C$_6$H$_4$ | CH$_2$CH$_2$N(CH$_3$)$_2$ | H | F | |
| 196 | 4-C$_6$H$_5$C$_6$H$_4$ | CH$_2$CH$_2$N(CH$_3$)$_2$.HCl | H | F | 80-84 |
| 197 | 4-(2-FC$_6$H$_4$)C$_6$H$_4$ | CH$_2$CH$_2$N(CH$_3$)$_2$ | H | F | 146-149 |
| 198 | 4-(2-FC$_6$H$_4$)C$_6$H$_4$ | CH$_2$CH$_2$N(CH$_3$)$_2$.HCl | H | F | 238(d) |
| 199 | 4-(2-FC$_6$H$_4$)C$_6$H$_4$ | (CH$_2$)$_3$N(CH$_3$)$_2$ | H | F | 88-92 |
| 200 | 4-(2-FC$_6$H$_4$)C$_6$H$_4$ | (CH$_2$)$_3$N(CH$_3$)$_2$.HCl | H | F | 118-123(d) |
| 201 | 4-(2-FC$_6$H$_4$)C$_6$H$_4$ | CH$_2$CH$_2$N(CH$_2$CH$_3$)$_2$ | H | F | 63-68 |
| 202 | 4-(2-FC$_6$H$_4$)C$_6$H$_4$ | CH$_2$CH$_2$N(CH$_2$CH$_3$)$_2$.HCl | H | F | 90-95(d) |
| 203 | 4-(2-FC$_6$H$_4$)C$_6$H$_4$ | CH$_2$CH$_2$N(CH$_3$)$_2$.HCl | Cl | H | |
| 204 | 4-(2-FC$_6$H$_4$)C$_6$H$_4$ | CH$_2$CH$_2$N(CH$_3$)$_2$.HCl | Cl | F | |
| 205 | 4-(4-CH$_3$C$_6$H$_4$)C$_6$H$_4$ | CH$_2$CH$_2$N(CH$_3$)$_2$.HCl | H | F | |
| 206 | 4-(4-BrC$_6$H$_4$)C$_6$H$_4$ | CH$_2$CH$_2$N(CH$_3$)$_2$.HCl | H | Cl | |

UTILITY

Results of the various biological tests described below establish that the compounds of this invention have the property of inhibiting not only the growth of transplanted mouse tumors but also the growth of human tumors implanted in mice.

The efficacy of the compounds of this invention against the transplanted mouse tumors was evaluated in test systems currently in use at the National Cancer Institute for the detection and assessment of anticancer activity. Most clinically effective drugs exhibit activity in these tests and the tests have a good record of predicting clinical efficacy [Goldin, A., Venditti, J. M., MacDonald, J. S., Muggia, F. M., Henney, J. E. and V. T. Devita, Jr., *Europ. J. Cancer*, 17, 129-142, (1981);

Venditti, J. M., *Seminars in Oncology*, 8 (4) (1981); Goldin, A. and J. M. Venditti, in *Recent Results in Cancer Research*, 70, S. K. Carter and Y. Sakurai, Eds., Springer-Verlag, Berlin/Heidelberg, 1980].

MELANOTIC MELANOMA B16 TEST

The animals used were $B_6C_3F_1$ mice, all of one sex, weighing a minimum of 18 g for males and 17 g for females and all within a 4 g weight range at the start of the test. The test group comprised 9 or 10 mice. The tumor was implanted in each of the test mice by the subcutaneous injection of 0.5 ml of a tumor homogenate prepared by homogenizing a 1 g portion of melanotic melanoma in 10 ml of cold physiological saline. The test compounds suspended in hydroxypropylcellulose were administered intraperitoneally at various doses once daily for nine consecutive days starting on day one relative to the day of tumor inoculation (day 0). The control mice received injections of hydroxypropylcellulose vehicle only. The mice were weighted and survivors were recorded on a regular basis for 60 days. The median survival times and the ratio of the median survival times for treated (T) to control (C) mice were calculated. The median survival time of the nontreated tumored mice ranged from 15 to 17 days. Drug effectiveness was assessed on the basis of the survival time. Results were expressed as a percentage of the control survival time (Survival Time T/C $\times$ 100%). The criterion for effectiveness was determined by: T/C $\times$ 100 $\geq$ 125 percent.

Results with the compound of Example 1 and cisplatin, a drug used clinically, are shown in Table 7. The data indicate that the compound of Example 1 is effective against the B16 melanoma in mice.

TABLE 7

Melanotic Melanoma B16 Test

| Compound | Dose (mg/kg) | T/C × 100 (percent) 2 Tests |
|---|---|---|
| Example 1 | 400 | 131, 179 |
|  | 200 | 145, 150 |
|  | 100 | 145, 155 |
|  | 50 | 148, 138 |
|  | 25 | 127, 125 |
| Cisplatin | 2 | 212, 136 |
|  | 1 | —, 175 |

Lymphoid Leukemia L1210

The animals used in this test were $CD_2F_1$ mice, all males weighing a minimum of 18 g and all within a 4 g weight range at the start of the test. The test group consisted of six mice. The tumor was implanted in each of the test mice by the intraperitoneal injection of 0.1 ml of diluted ascitic fluid containing $10^5$ cells drawn from a mouse with L1210 leukemia. The test compounds were suspended in hydroxypropylcellulose or saline with Tween ® 80 surfactant or dissolved in saline and injected intraperitoneally, at various doses, once daily for nine consecutive days starting on day one relative to the day of tumor inoculation (day 0). The control mice received injections of saline or hydroxypropylcellulose vehicle only. The mice were weighed and survivors were recorded on a regular basis for 30 days. The median survival time and the ratio of the median survival time for the treated (T) and control (C) mice was calculated. The median survival time of the nontreated tumored mice ranged from 8-9 days. Drug effectiveness was assessed on the basis of the survival time. Results were expressed as a percentage of the control survival time (Median Survival Time: T/C $\times$ 100%). The criterion for effectiveness was determined by: T/C $\times$ 100 $\geq$ 125 percent.

Results of tests with compounds of this invention are shown in Table 8. The data indicate that the compounds of the invention are effective against the L1210 leukemia in mice.

HUMAN COLON TUMOR TEST IN VITRO

The compound of this invention were also tested for their ability to inhibit the growth of human colon carcinoma cells in vitro. Compounds effective in inhibiting the growth of these cells also show activity in inhibiting the L1210 leukemia in mice.

The human colon carcinoma cells, designated HCT-15, were derived from a specimen of an adenocarcinoma of human colon removed during surgery. The cells were grown in Roswell Park Medical Institute (RPMI) Medium 1640 supplemented with 10% heat inactivated fetal calf serum, penicillin (100 units/ml), streptomycin (100 $\mu$g/ml), gentamicin (20 $\mu$g/ml), fungizone (25 $\mu$g/ml), 0.075 percent sodium bicarbonate, 10 $\mu$M 4-(2-hydroxyethyl)-1-piperazineethanesulfonic acid and 10 $\mu$M N-tris(hydroxymethyl)methylglycine. To determine the potency of the test compounds in inhibiting the growth of the cells, the procedure was as follows: On day 0, replicate 35 mm tissue culture dishes were each inoculated with $1.5 \times 10^5$ HCT-15 cells in 2 ml supplemented RPMI Medium 1640. On day 1 cells from sample dishes were harvested using trypsin (0.25%) treatment and counted with a hemocytometer to determine the number of cells per dish at the time of the addition of the compounds. Compounds of this invention were added in varying concentrations to other cultures. On day 4, treated and control cultures were harvested by trypsin treatment and the number of cells was determined. The number of doublings for the control cells was determined from the cell numbers on days 1 and 4. The $ID_{50}$, the concentration of compound required to inhibit by 50 percent the number of doublings, was then calculated from the dose-response curve in which cell numbers were plotted on log-log paper against compound concentrations in micrograms per ml. Results of tests with compounds of this invention and with reference drugs used clinically are shown in Table 8. They show that the compounds are active in inhibiting the growth of the human colon tumor cells.

TABLE 8

| Example No. | L1210 Leukemia (dose in mg/kg) % T/C | in vitro HCT-15 ID50 µg/ml |
|---|---|---|
| 1 | (200) 189 | 0.05 |
| 2 | (50) 186 | 0.10 |
| 3 | (400) 207 | 0.50 |
| 4 | (200) 128 | 0.48 |
| 5 | (400) 141 | 0.02 |
| 6 | (400) 162 | 0.24 |
| 7 | (200) 136 | 2.30 |
| 8 | (400) 147 | 0.40 |
| 9 | (200) 127 | 0.07 |
| 10 | (200) 163 | 0.03 |
| 11 | (25) 176 | 0.19 |
| 12 | (50) 261 | 1.00 |
| 13 | (400) 129 | 0.24 |
| 14 | (50) 195 | 0.38 |
| 15 | (200) 158 | 0.28 |
| 16 | (400) 190 | 1.00 |
| 17 | (400) 136 | 0.65 |
| 18 | (100) 185 | <0.50 |
| 19 | (25) 234 | <0.50 |

TABLE 8-continued

| Example No. | L1210 Leukemia (dose in mg/kg) % T/C | in vitro HCT-15 ID50 μg/ml |
|---|---|---|
| 20 | (200) 211 | <0.50 |
| 21 | (200) 160 | <5.0 and >0.5 |
| 22 | (100) 135 | <5.0 and >0.5 |
| 23 | (25) 159 | <5.0 and >0.5 |
| 24 | (400) 154 | 0.28 |
| 26 | (300) 136 | <0.50 |
| 27 | (50) 155 | NT |
| 28 | (18) 174 | <0.50 |
| 29 | (18) 194 | <0.50 |
| 30 | (300) 291 | <0.50 |
| 31 | (37.5) 218 | <0.50 |
| 32 | (175) 153 | <5.0 and >0.5 |
| 33 | (200) 170 | <0.50 |
| 34 | (400) 170 | NT |
| 35 | (150) 204 | NT |
| 36 | (75) 185 | NT |
| 37 | (50) 155 | NT |
| 38 | (200) 238 | >1 |
| 39 | NT | <0.1 |
| 40 | (100) 157 | >1 |
| 41 | NT | $7.9 \times 10^{-3}$ |
| 44 | (100) 136 | <0.1 |
| 45 | (400) 160 | 0.13 |
| 46 | NT | 0.42 |
| 47 | NT | 3.20 |
| 48 | NT | 0.10 |
| 49 | (200) 174 | >5.00 |
| 50 | (100) 131 | >5.00 |
| 51 | (75) 173 | <0.50 |
| 52 | (75) 189 | <0.50 |
| 53 | (75) 136 | <0.50 |
| 54 | (300) 125 | <0.50 |
| 55 | (150) 156 | <5.0 and >0.5 |
| 56 | (75) 176 | <0.50 |
| 57 | (150) 197 | <0.50 |
| 58 | (150) 141 | >0.50 |
| 59 | (300) 152 | >5.00 |
| 60 | (300) 192 | <0.50 |
| 61 | (75) 160 | NT |
| 68 | (100) 162 | <1 and >0.1 |
| 70 | NT | <0.1 |
| 71 | (25) 163 | <1.0 and >0.1 |
| 73 | (50) 195 | <0.1 |
| 74 | (50) 104 | NT |
| 75 | (150) 145 | NT |
| 76 | (200) 179 | <1.0 and >0.1 |
| 80 | (25) 128, 196 | <0.50 |
| 81 | (25) 191 | <0.50 |
| 82 | (100) 144 | >1.00 |
| 83 | (100) 198 | >1.00 |
| 84 | NT | <0.1 |
| 85 | (100) 184 | <1 and >0.1 |
| 86 | (175) 153 | <5.0 and >0.50 |
| 87 | (100) 146 | <0.50 |
| 91 | (100) 103 ≠ (40) 140* | 0.04 |
| 92 | (50) 180, 176, 172 | 0.03 |
| 93 | (50) 101≠ | 0.06, 0.04 |
| 94 | (100) 107≠ | 0.65 |
| 95 | (100) 108≠ | 0.04 |
| 96 | (37.5) 97≠ | <0.50 |
| 97 | (25) 110≠ | 0.14 |
| 99 | (50) 101≠ | 0.07, 0.34 |
| 100 | (50) 103≠ | 0.028, 0.24 |
| 101 | (50) 154, 161 | 0.41 |
| 102 | (12.5) 164 | 1.0, 1.9 |
| 103 | (200) 108≠ | 0.17 |
| 104 | (100) 137, 164 | 0.22 |
| 105 | (12.5) 108≠ | 0.33 |
| 106 | (25) 107≠ | 1.20 |
| 107 | (25) 116≠ | 0.09 |
| 108 | (100) 166 | 0.10 |
| 109 | (100) 172 | <0.50 |
| 110 | (25) 135 | <0.50 |
| 111 | (25) 125, 135 | <0.50 |
| 112 | (25) 128 | <0.50 |
| 113 | (25) 166, 166 | <5.0 and >0.5 |
| 114 | (50) 121≠ | 1.30 |
| 116 | (75) 102≠ | <0.50 |
| 117 | (25) 163, 175 | <5.0 and >0.5 |
| 118 | (25) 179, 195 | 0.017 |
| 119 | (18) 170 | <0.50 |
| 120 | (100) 132 | <0.50 |
| 121 | (18) 175 | <0.50 |
| 122 | (175) 153 | <5.0 and >0.5 |
| 123 | (21.9) 145 | <0.50 |
| 124 | (360) 184 | NT |
| 125 | (150) 150 | NT |
| 126 | (37.5) 150 | NT |
| 127 | (50) 193 | NT |
| 128 | (25) 135 | >1 |
| 129 | (100) 154 | <0.1 |
| 130 | (50) 132 | >1.0 |
| 134 | (100) 110≠ | <1 and >0.1 |
| 135 | (400) 160 | 0.13, 0.55 |
| 136 | (25) 103≠ | >0.50 |
| 137 | (50) 107≠ | >5.00 |
| 139 | (100) 146 | <5.00 |
| 141 | (75) 139 | <0.50 |
| 142 | (37.5) 169 | <0.50 |
| 143 | (37.5) 132 | <0.50 |
| 144 | (37.5) 123≠ | <0.50 |
| 145 | (75) 132 | <0.50 |
| 146 | (37.5) 164 | <0.50 |
| 147 | (18) 132 | <0.50 |
| 148 | (37.5) 102≠ | >5.00 |
| 149 | (75) 107≠ | >5.00 |
| 150 | (37.5) 105≠ | <0.50 |
| 151 | (75) 144 | <5.0 and >0.5 |
| 158 | (100) 148 | <1 and >0.1 |
| 160 | (25) 174 | <0.1 |
| 161 | (100) 148 | >1.00 |
| 163 | (43.8) 180 | <0.50 |
| 164 | (22.5) 234 | <0.50 |
| 165 | (50) 128 | >1.00 |
| 166 | (50) 156 | <1.0 and >0.1 |
| 167 | (12.5) 197 | <0.1 |
| 168 | (100) 148 | 0.04 |
| 169 | NT | 0.04 |
| 170 | (25) 188 | 0.10 |
| 171 | (100) 164 | <0.50 |
| 172 | (100) 151 | <0.50 |
| 173 | (25) 122≠ | <0.50 |
| 174 | (12.5) 156, 159 | <5 and >0.5 |
| 175 | (12.5), 156, 159 | <5.0 and >0.5 |
| 176 | (37) 175 | <0.50, 0.41 |
| 177 | (37.5) 172 | <0.50 |
| 178 | (75) 172 | <0.50 |
| 179 | (37.5) 166 | <0.50 |
| 180 | (18) 101≠ | <0.50 |
| 181 | (37.5) 108≠ | <0.50 |
| 182 | (46) 168 | <0.50 |
| 183 | (22.5) 208 | <5.0 and >0.5 |
| 184 | (175) 153 | <5.0 and >0.5 |
| 185 | (50) 175 | <1.0 and >0.1 |
| 186 | (45) 123≠ | <0.50 |
| 187 | (75) 131 | <0.50 |
| 188 | (12.5) 187 | <0.01 |
| 189 | (12.5) 197 | <0.1 |
| 190 | (50) 195 | <1.0 and >0.1 |
| 191 | (200) 156, 132 | NT |
| 192 | (200) 166 | >1 |
| 196 | (50) 205 | <1.0 and >0.1 |
| 197 | (50) 179 | <0.01 |
| 198 | (100) 178 | $<10^{-3}$ |
| 199 | (25) 153 | NT |
| 200 | (25) 140 | NT |
| 201 | (100) 175 | >1.0 |
| 202 | (59) 164 | >1.0 |
| 207 | (25) 154 | .02 |
| 208 | NT | $<10^{-3}$ |
| 210 | (25) 177 | .03 |
| 211 | NT | $<10^{-3}$ |
| Adriamycin | (2) 183 | 0.01 |
| Cisplatin | NT | 0.66 |
| 5-Fluoroura- | (16) 228 | 0.27 |

TABLE 8-continued

| Example No. | L1210 Leukemia (dose in mg/kg) % T/C | in vitro HCT-15 ID50 μg/ml |
|---|---|---|
| cil | | |

≠=Compounds dosed at non-optimal Q1DX9 instead of Q3DX9, should be active if dosed Q3DX9.
NT = not tested The compounds of Example 1 and 91 were also tested for effectiveness against a human colon tumor implanted in athymic mice. These mice are immunodeficient and thus do not reject implanted tumors of human origin.

HUMAN COLOR TUMOR HCT-15

The animals used were Swiss NU/NU athymic mice, weighing 20–22 g each at the start of the test. The test group consisted of twelve mice, seven males and five females. The HCT-15 tumor cell line, derived from a patient with adenocarcinoma of the colon, was maintained in culture. The tumor was implanted in each of the test mice by the subcutaneous injection in the flank region of 0.2 ml of physiological saline containing $10^7$ HCT-15 cultured cells. Tumors appeared within 72 hours and treatment started one week after tumor inoculation.

Test compounds, suspended in methocel (0.5% in water) or dissolved in water, were injected intraperitoneally once daily for five consecutive days starting on day seven relative to the day of tumor inoculation (day 0). The body weight and the size of the tumor were determined daily. Tumor size was determined by two-dimensional caliper measurements. Tumor weight was estimated from the formula:

$$\frac{1 \times w^2}{2} = mg$$

tumor weight in which l = length and w = width of the tumor in mm. The net tumor weight was determined by subtracting from the actual tumor weight at the time of evaluation the initial estimated tumor weight at the time treatment was started (day 7). Drug effectiveness was assessed on the basis of inhibition of the gain in net tumor weight in the treated (T) compared to that of the control (C) mice. Percent tumor growth inhibition was calculated by the formula:

$$\text{Percent tumor growth inhibition} = \left[1 - \frac{\text{net tumor weight: Treated}}{\text{net tumor weight: Control}}\right] \times 100\%.$$

Results of a test are shown in Table 9. The data indicate that the compounds of this invention inhibited the growth of the HCT-15 human colon tumor in mice. 5-Fluorouacil used as a reference drug was toxic at the 40 mg/kg dose and ineffective at the 20 mg/kg dose. 5-Fluorouracil is sometimes used in the treatment of colon tumors in man but is not consistently effective.

TABLE 9

Human Colon Tumor HCT-15 In Mice

| Compound | Dose mg/kg | Day 7* Average Tumor Weight (mg) | Day 21 Average Tumor Weight (mg) | Day 21 Net Tumor Weight gain (mg) | Day 21 Tumor Growth Inhibition (Percent) |
|---|---|---|---|---|---|
| Methocel Control | 0 | 56.2 | 349.9 | 293.7 | 0 |
| Example 1 | 200 | 56.8 | 156.3 | 99.4 | 66.2 |
| | 100 | 56.6 | 212.9 | 156.3 | 46.8 |
| | 50 | 56.3 | 252.9 | 196.6 | 33.1 |
| Example 91 | 40 | 56.8 | 256.9 | 200.1 | 32.0 |
| | 20 | 56.2 | 245.1 | 188.9 | 35.7 |
| | 10 | 56.8 | 322.8 | 266.0 | 10.0 |
| 5-Fluorouracil | 40 | | Toxic | | |
| | 20 | 56.7 | 421.7 | 365 | 0 |

*Day treatment was started.

In summary, tests have shown that the compounds of this invention have antitumor activity against transplanted mouse tumors including the L1210 lymphoid leukemia and the B16 melanotic melanoma, in mice. The compounds are also active against the human colon tumor HCT-15 in tissue culture or xenografted in athymic mice.

DOSAGE FORMS

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms, kind of concurrent treatment, frequency of treatment, and the effect desired. Usually a daily dosage of active ingredient can be about 5 to 400 milligrams per kilogram of body weight. Ordinarily 10 to 200, and preferably 10 to 50 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A method of treating lymphoid leukemia in a mammal which comprises administering to a mammal an effective amount of at least one compound having the formula:

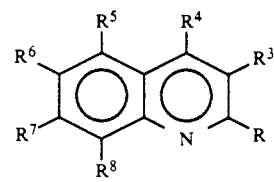

wherein
R is

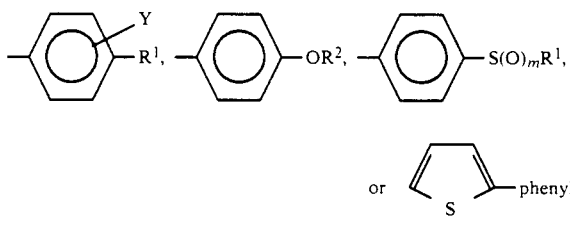

$R^1$ is $CH_3CH_2(CH_3)CH$, alkyl of 5-12 carbon atoms, cyclohexyl,

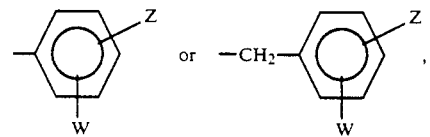

when
R is $R^2$ can be in

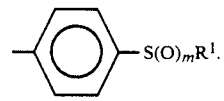

addition alkyl of 3-4 carbon atoms;
$R^2$ is

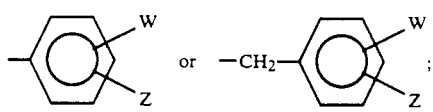

$R^3$ is H, alkoxy of 1-3 carbon atoms, or alkyl of 1-2 carbon atoms;
$R^4$ is $CO_2H$ or $CO_2R^{11}$;
$R^5$, $R^6$, $R^7$ and $R^8$ are independently H, F, Cl, Br, I, $CH_3$, $CF_3$, $SCH_3$ or $CH_2CH_3$, at least two of $R^5$, $R^6$, $R^7$, and $R^8$ being H;
$R^9$ and $R^{9A}$ are independently H or alkyl of 1 to 3 carbon atoms;
$R^{11}$ is $(CH_2)_{2-4}NR^9R^{9A}$;

W, Y and Z are independently H, F, Cl, Br, alkyl of 1-5 carbon atoms, $NO_2$, OH, $CF_3$ or $OCH_3$;

m is 0 or 1; or a pharmaceutically suitable salt thereof;

with the following provisos:

1) $R^5$, $R^6$ and $R^7$ cannot all be H;

2) when $R^4$ is $CO_2CH_2CH_2N(CH_3)_2$, $R^6$ is $CH_2CH_3$, or $R^7$ is Cl, $R^1$ cannot be cyclohexyl;

3) when $R^1$ is cyclohexyl and $R^3$ is H, $R^6$ must be Cl or F, but $R^6$ and $R^8$ cannot both be Cl; and 4) when $R^6$ is $CH_3$, then $R^7$ cannot be Cl.

2. The method of claim 1 wherein the compound has the formula:

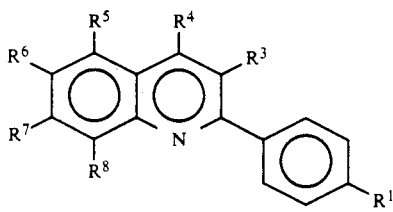
(II)

wherein $R^1$ is cyclohexyl; phenyl; phenyl substituted with one halogen, alkyl of 1-5 carbon atoms or $CF_3$, phenoxy; or phenoxy substituted with one halogen or alkyl of 1-5 carbon atoms;

$R^3$ is H or alkyl of 1-2 carbon atoms;

$R^4$ is $CO_2H$, a sodium or potassium salt thereof, or $CO_2R^{11}$;

$R^5$ and $R^6$ are independently H, halogen, $CH_3$ or $CF_3$;

$R^7$ and $R^8$ are independently H or halogen;

$R^{11}$ is $(CH_2)_{2-4}NR^9R^{9A}$; and $R^9$ and $R^{9A}$ are independently alkyl of 1 to 3 carbon atoms;

or a pharmaceutically suitable salt thereof;

provided that $R^5$, $R^6$ and $R^7$ cannot all be H and that when $R^1$ is cyclohexyl and $R^3$ is H, $R^6$ must be Cl or F, but $R^6$ and $R^8$ cannot both be Cl.

3. The method of claim 1 wherein the compound has the formula:

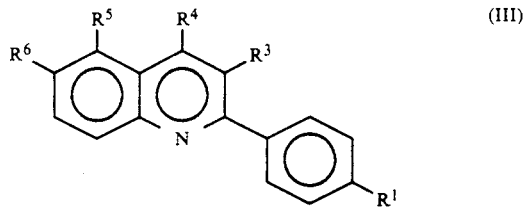
(III)

wherein
$R^1$ is cyclohexyl,

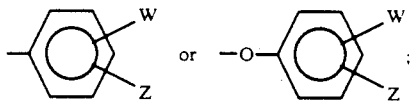

$R^3$ is H or alkyl of 1-2 carbon atoms;
$R^4$ is $CO_2H$, a sodium or potassium salt thereof, or $CO_2R^{11}$;
$R^5$ and $R^6$ are independently H, halogen or $CF_3$ provided that both $R^5$ and $R^6$ are not hydrogen;
$R^{11}$ is $(CH_2)_{2-4}NR^9R^{9A}$;
$R^9$ and $R^{9A}$ are independently alkyl of 1 to 3 carbon atoms; and
W and Z are independently H, halogen, alkyl of 1-5 carbon atoms or $CF_3$;
provided that when $R^1$ is phenyl or phenoxy, and $R^5$ is H, then $R^6$ cannot be Br and that when $R^1$ is cyclohexyl and $R^3$ is H, $R^6$ must be Cl or F.

4. The method of claim 3 wherein in the compound
$R^1$ is phenyl, phenyl substituted with at least one halogen, phenoxy, or phenoxy substituted with at least one halogen;
$R^3$ is methyl;
$R^5$ is H or Cl; and
$R^6$ is H, F or Cl.

5. The method of claim 1 wherein the compound is 2-(1,1'-biphenyl-4-yl)-6-fluoro-3-methyl-4-quinolinecarboxylic acid, sodium or potassium salt.

6. The method of claim 1 wherein the compound is 6-fluoro-3-methyl-2-(4-phenoxyphenyl)-4-quinolinecarboxylic acid, sodium or potassium salt.

7. The method of claim 1 wherein the compound is 2-(4'-bromo-1,1'-biphenyl-4-yl)-6-fluoro-3-methyl-4-quinolinecarboxylic acid, sodium or potassium salt.

8. The method of claim 1 wherein the compound is 2-(2'-fluoro-1,1'-biphenyl-4-yl)-6-fluoro-3-methyl-4-quinolinecarboxylic acid, sodium or potassium salt.

9. The method of claim 1 wherein the compound is 2-(1,1'-biphenyl-4-yl)-5-chloro-6-fluoro-3-methyl-4-quinolinecarboxylic acid, sodium or potassium salt.

10. The method of claim 1 wherein the compound is [6-fluoro-2(2'-fluoro-1,1'-biphenyl-4-yl)-3-methyl-[(2-dimethylamino)ethyl]ester-4-quinolinecarboxylic acid]-hydrochloride.

11. The method of claim 1 wherein the compound is 2-(1,1'-biphenyl-4-yl)-5-chloro-3-methyl-4-quinolinecarboxylic acid, sodium or potassium salt.

* * * * *